United States Patent
Tockman et al.

(10) Patent No.: US 8,442,656 B2
(45) Date of Patent: *May 14, 2013

(54) CARDIAC LEAD HAVING IMPLANTABLE STIFFENING STRUCTURES FOR FIXATION

(75) Inventors: Bruce A. Tockman, Scandia, MN (US); Brian D. Soltis, St. Paul, MN (US); Eric T. Johnson, Temecula, CA (US); Kent C. B. Stalker, San Marcos, CA (US); Peter J. D'aquanni, Murrieta, CA (US); Paul E. Zarembo, Vadnais Heights, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 2084 days.

This patent is subject to a terminal disclaimer.

(21) Appl. No.: 11/422,014

(22) Filed: Jun. 2, 2006

(65) Prior Publication Data

US 2007/0282415 A1 Dec. 6, 2007

(51) Int. Cl.
*A61N 1/05* (2006.01)

(52) U.S. Cl.
USPC ........... 607/122; 607/115; 607/116; 607/119; 607/125

(58) Field of Classification Search ................... 607/122, 607/126
See application file for complete search history.

(56) References Cited

U.S. PATENT DOCUMENTS

| | | | |
|---|---|---|---|
| 4,046,151 A | * | 9/1977 | Rose ............................. 607/127 |
| 4,217,913 A | | 8/1980 | Dutcher |
| 4,467,817 A | * | 8/1984 | Harris ........................... 607/122 |
| 4,493,329 A | * | 1/1985 | Crawford et al. ............. 607/125 |
| 5,507,751 A | * | 4/1996 | Goode et al. .................. 606/108 |
| 5,571,135 A | | 11/1996 | Fraser et al. |
| 5,674,273 A | * | 10/1997 | Helland ......................... 607/122 |
| 5,769,077 A | * | 6/1998 | Lindegren ..................... 600/373 |

(Continued)

FOREIGN PATENT DOCUMENTS

| | | |
|---|---|---|
| EP | 1832309 A2 | 9/2007 |
| JP | 10500873 A | 1/1998 |
| JP | 2002503531 A | 2/2002 |
| JP | 2005536262 A | 12/2005 |

OTHER PUBLICATIONS

International Search Report and Written Opinion of International Application No. PCT/US2007/067886, filed May 1, 2007, both mailed Oct. 16, 2007, 10 pages.

(Continued)

*Primary Examiner* — Carl H Layno
*Assistant Examiner* — Erin Piateski
(74) *Attorney, Agent, or Firm* — Faegre Baker Daniels LLP

(57) ABSTRACT

A cardiac lead adapted for fixation at least partially within a cardiac vessel. The lead includes, in one embodiment, an elongate lead body defining a proximal region and a distal region including a distal end region having at least one electrode and a distal tip. The distal end region is configured such that the electrode and the distal tip can be implanted in the cardiac vessel. Stiffening structures in the distal region of the lead are adapted to stiffen selected portions of the lead for fixation of the electrode within the cardiac vessel. In some embodiments, the stiffening structures include an implantable member adapted to be implanted in a lumen of the lead. In other embodiments, the stiffening structures include a sheath adapted to be deployed over the lead body. In still other embodiments, the stiffening structures are integral to the lead and/or the lead body.

23 Claims, 15 Drawing Sheets

U.S. PATENT DOCUMENTS

| | | | |
|---|---|---|---|
| 5,769,858 A | 6/1998 | Pearson et al. | |
| 5,800,497 A * | 9/1998 | Bakels et al. | 607/122 |
| 5,925,073 A | 7/1999 | Chastain et al. | |
| 5,951,597 A | 9/1999 | Westlund et al. | |
| 6,021,340 A * | 2/2000 | Randolph et al. | 600/381 |
| 6,126,635 A * | 10/2000 | Simpson et al. | 604/101.05 |
| 6,136,021 A | 10/2000 | Tockman et al. | |
| 6,156,053 A * | 12/2000 | Gandhi et al. | 606/194 |
| 6,249,708 B1 * | 6/2001 | Nelson et al. | 607/122 |
| 6,408,214 B1 * | 6/2002 | Williams et al. | 607/122 |
| 6,447,507 B1 * | 9/2002 | Bednarek et al. | 606/41 |
| 6,510,348 B2 | 1/2003 | Clemens et al. | |
| 6,549,812 B1 | 4/2003 | Smits | |
| 6,556,873 B1 | 4/2003 | Smits | |
| 6,562,049 B1 * | 5/2003 | Norlander et al. | 606/108 |
| 6,638,268 B2 * | 10/2003 | Niazi | 604/528 |
| 6,666,826 B2 | 12/2003 | Salo et al. | |
| 6,718,211 B2 | 4/2004 | Smits | |
| 6,728,579 B1 | 4/2004 | Lindgren et al. | |
| 6,733,500 B2 * | 5/2004 | Kelley et al. | 606/41 |
| 6,741,893 B2 | 5/2004 | Smits | |
| 6,776,765 B2 * | 8/2004 | Soukup et al. | 600/585 |
| 6,887,229 B1 * | 5/2005 | Kurth | 604/525 |
| 6,968,237 B2 * | 11/2005 | Doan et al. | 607/122 |
| 6,970,748 B2 | 11/2005 | Haldeman et al. | |
| 7,025,766 B2 * | 4/2006 | Whayne et al. | 606/41 |
| 2002/0072787 A1 | 6/2002 | Partridge et al. | |
| 2003/0045919 A1 * | 3/2003 | Swoyer et al. | 607/122 |
| 2003/0130581 A1 | 7/2003 | Salo et al. | |
| 2003/0181967 A1 * | 9/2003 | Dadd et al. | 607/122 |
| 2003/0195602 A1 * | 10/2003 | Boling | 607/122 |
| 2003/0204138 A1 * | 10/2003 | Choi | 600/434 |
| 2003/0204231 A1 * | 10/2003 | Hine et al. | 607/122 |
| 2003/0220677 A1 * | 11/2003 | Doan et al. | 607/122 |
| 2004/0039371 A1 | 2/2004 | Tockman et al. | |
| 2004/0215139 A1 * | 10/2004 | Cohen | 604/95.04 |
| 2004/0254600 A1 | 12/2004 | Zarbatany et al. | |
| 2004/0260371 A1 | 12/2004 | Greenland et al. | |
| 2005/0015048 A1 * | 1/2005 | Chiu et al. | 604/101.04 |
| 2005/0165388 A1 * | 7/2005 | Bhola | 606/14 |
| 2005/0222678 A1 * | 10/2005 | Lashinski et al. | 623/2.11 |
| 2007/0282413 A1 | 12/2007 | Tockman et al. | |

OTHER PUBLICATIONS

International Search Report and Written Opinion issued in PCT/US2007/067886, mailed Oct. 16, 2007, 10 pages.

International Search Report and Written Opinion issued in PCT/US2007/067887, mailed Nov. 5, 2007, 12 pages.

* cited by examiner

CARDIAC LEAD HAVING IMPLANTABLE STIFFENING STRUCTURES FOR FIXATION

CROSS-REFERENCE TO RELATED APPLICATIONS

The present application is related to co-pending U.S. patent application Ser. No. 11/422,012 entitled "CARDIAC LEAD HAVING STIFFENING STRUCTURES FOR FIXATION" and filed as the same date as the present application by Bruce A. Tockman, et al. The above-identified application is incorporated herein by reference for all purposes.

TECHNICAL FIELD

The present invention relates to devices and methods for fixation of medical electrical leads. In particular, the present invention is directed to devices and methods for atraumatic fixation of a portion of a cardiac lead within a cardiac vessel.

BACKGROUND

Implantable medical devices for treating irregular contractions of the heart with electrical stimuli are known. Exemplary implantable devices are defibrillators and pacemakers. Various types of electrical leads for defibrillators and pacemakers have been suggested, many of which are placed transvenously. Such leads are introduced into the patient's vasculature at a venous access site and travel through veins to the sites where the leads' electrodes will be implanted or otherwise contact target coronary tissue. Electrodes for transvenously-placed leads can be implanted in the endocardium (the tissue lining the inside of the heart) of the right atrium or ventricle, or alternatively, in the branch vessels of the coronary venous system. In particular, lead electrodes can be implanted in the coronary sinus or a branch vessel thereof for sensing and/or stimulation of the left side of the heart (i.e., the left ventricle).

Various techniques have been used to facilitate fixation of the foregoing types of leads at the desired implantation sites. For leads partially implanted within the coronary venous system, fixation techniques should be substantially atraumatic and yet provide fixation sufficient to withstand natural heart motion and retrograde blood flow which naturally tend to push the lead out of the branch vessel into which the electrode is implanted. Additionally, it is desirable to permit and facilitate partial or complete removal of the lead and fixation structures after implantation if necessary or desired.

Accordingly, there is a continuing need for improved devices and methods for fixation of cardiac leads in the coronary venous systems. In particular, there is a need in the art for a fixation approach that effectively secures the lead electrodes in the target coronary branch vessel while still permitting subsequent removal of the lead.

SUMMARY

The present invention, in one embodiment, is an implantable medical electrical lead assembly. The lead assembly comprises a medical electrical lead that is adapted to be connected at a proximal end to an implanted medical device, and has a length sufficient to extend at least from an implantation location of the implanted medical device and into a branch vessel of a coronary sinus of a patient. The lead includes a first region associated with the branch vessel, and a second region associated with the coronary sinus. The assembly further comprises an implantable stiffening structure coupled to the lead. At least a portion of the stiffening structure is located in a selected portion of the first region. The stiffening structure is adapted to be coupled to the lead after positioning the first region within the branch vessel.

In another embodiment, the present invention is an implantable medical electrical lead assembly, comprising a medical electrical lead adapted to be connected at a proximal end to an implanted medical device. The lead has a length sufficient to extend at least from an implantation location of the implanted medical device to a location within a cardiac vessel. The lead includes a proximal region, and a distal region having a distal end region adapted for implantation within the cardiac vessel. The lead assembly further comprises an implantable stiffening means coupled to the lead for stiffening at least a first selected portion of the lead to cause fixation of the distal end region within the cardiac vessel.

The present invention, in yet another embodiment, is a method for fixation of a portion of a medical electrical lead within a cardiac vessel. The lead includes a distal region having a distal end region. The method comprises first transvenously delivering the lead to an implanted position such that the distal end region is positioned within the cardiac vessel. The method further includes next advancing an implantable stiffening structure along the lead after delivering the lead to the implanted position. The method then includes coupling the stiffening structure to the lead so as to stiffen a first selected location of the lead to cause fixation of the distal end region within the cardiac vessel.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
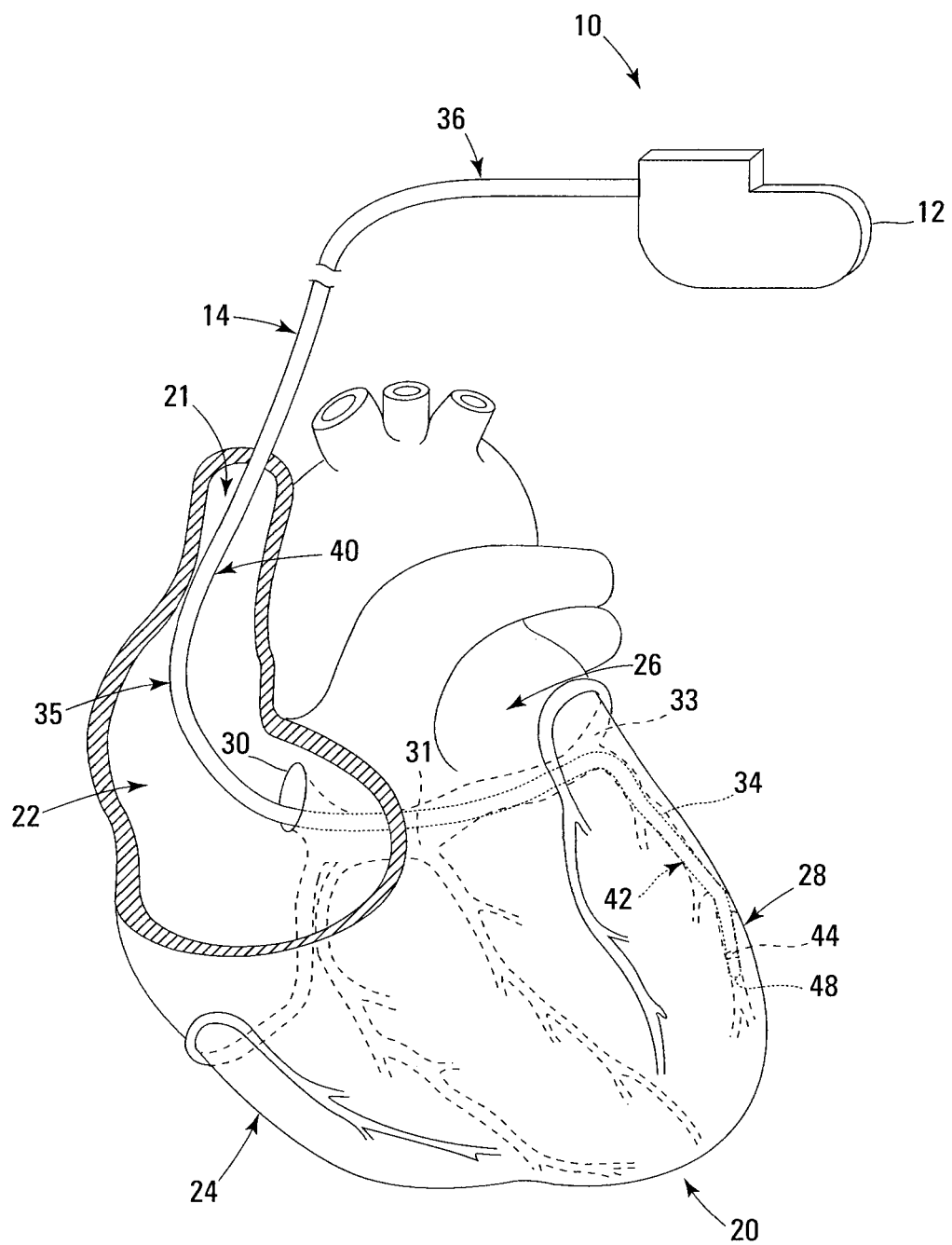
FIG. 1 is a schematic drawing of a cardiac rhythm management system including a pulse generator coupled to a lead deployed in a patient's heart according to one embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic drawing of a cardiac rhythm management system 10 including a pulse generator 12 coupled to a lead 14 deployed in a patient's heart 20 from a superior vena cava 21. As is known in the art, the pulse generator 12 is typically implanted subcutaneously at an implantation location in the patient's chest or abdomen. As shown, the heart 20 includes a right atrium 22 and a right ventricle 24, a left atrium 26 and a left ventricle 28, a coronary sinus ostium 30 in the right atrium 22, a coronary sinus 31, and various cardiac branch vessels including a great cardiac vein 33 and an exemplary branch vessel 34.

As shown in FIG. 1, the lead 14 includes an elongate body 35 defining a proximal region 36 and a distal region 40. The distal region 40 has a distal end region 42 including at least one electrode 44 and terminating in a distal tip 48. In the embodiment illustrated in FIG. 1, the distal region 40 is guided through the superior vena cava 21, the right atrium 22, the coronary sinus ostium 30, and the coronary sinus 31, and into the branch vessel 34 of the coronary sinus 31, with the distal end region 42, and thus the electrode 44 and the distal tip 48, positioned within the branch vessel 34. The illustrated position of the lead 14 may be used, for example, for sensing physiologic parameters and delivering a pacing and/or defibrillation stimulus to the left side of the heart 20. The lead 14 may also be partially deployed in other cardiac vessels such as the great cardiac vein 33 or other branch vessels for providing therapy to the left side (or other portions) of the heart 20.

Figure 2:
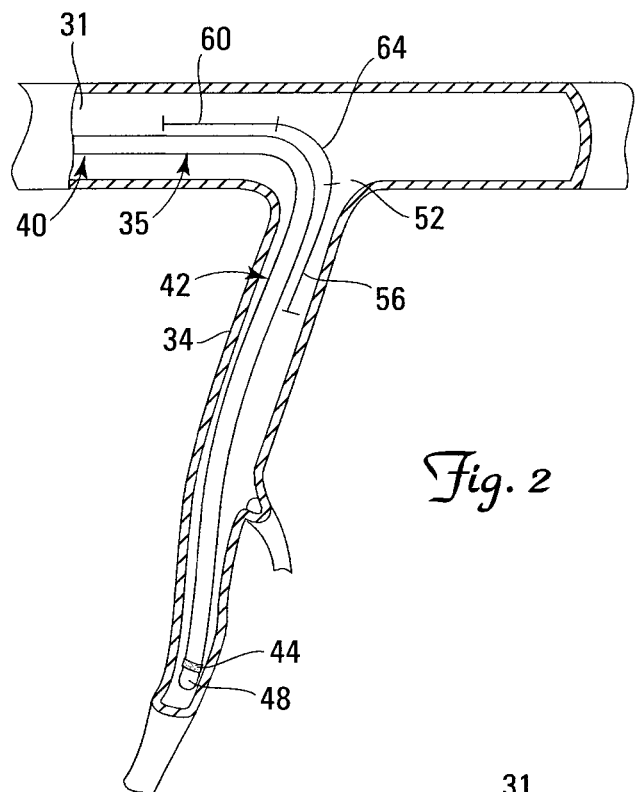
FIG. 2 is a partial cutaway view of a cardiac vessel showing a distal region of a lead partially implanted therein.

FIG. 2 is a partial cutaway view of the branch vessel 34 and the coronary sinus 31 showing a portion of the distal region 40 the lead 14 in an implanted position, with the distal end region 42 positioned within the branch vessel 34. As shown in FIG. 2, the distal region 40 extends from the coronary sinus 31 through an entrance 52 of the branch vessel 34 and into the branch vessel 34. As further shown, in the implanted position of FIG. 2, the electrode 44 is disposed within the branch vessel 34 such that it can deliver a therapeutic stimulus (e.g., a pacing and/or defibrillation stimulus) to the cardiac tissue.

The implanted position of FIG. 2 defines first, second, and third selected fixation portions 56, 60, and 64, respectively, of the lead 14. As shown, in the implanted position, the first fixation portion 56 occupies a position within the branch vessel 34 with the second fixation portion 60 positioned proximal the entrance 52 of the branch vessel 34, and the third fixation portion 64 extending between the first and second portions 56, 60 and through the entrance 52 of the branch vessel 34.

Portions of the lead 14, and in particular, the fixation portions 56, 60, and 64, can be selectively changed between a first or flexible state for delivery of the lead 14 to the implanted position (and subsequent removal of the lead 14 from the implanted position, if desired), and a second or stiffened state for fixation of the distal end region 42, and in particular, the distal tip 48 and electrode 44, within the branch vessel 34. When the portions 56, 60 and 64 are in the flexible state, the lead 14 is sufficiently flexible that it can be navigated through the right atrium 22 and the coronary venous system using tools and techniques (e.g., guide catheters, guide wires) known in the art. Once delivered to the implantation position as shown in FIGS. 1 and 2, the flow of blood (which is in the direction from the branch vessel 34 into the coronary sinus 31), and normal cardiac motion can have the effect of pushing the distal end region 42 out of the branch vessel 34. Selectively stiffening the fixation portions 56, 60, and/or 64 of the lead (i.e., changing these portions to the second or stiffened state) can prevent or significantly impede the spontaneous motion of the distal end region 42 in the direction of the entrance 52 of the branch vessel 34, thus requiring an external force to remove the distal end region 42 from the branch vessel 34. The fixation portions 56, 60, and/or 64 can be stiffened (i.e., changed from the flexible state to the stiffened state) utilizing stiffening structures illustrated and discussed in detail below.

Figure 3:
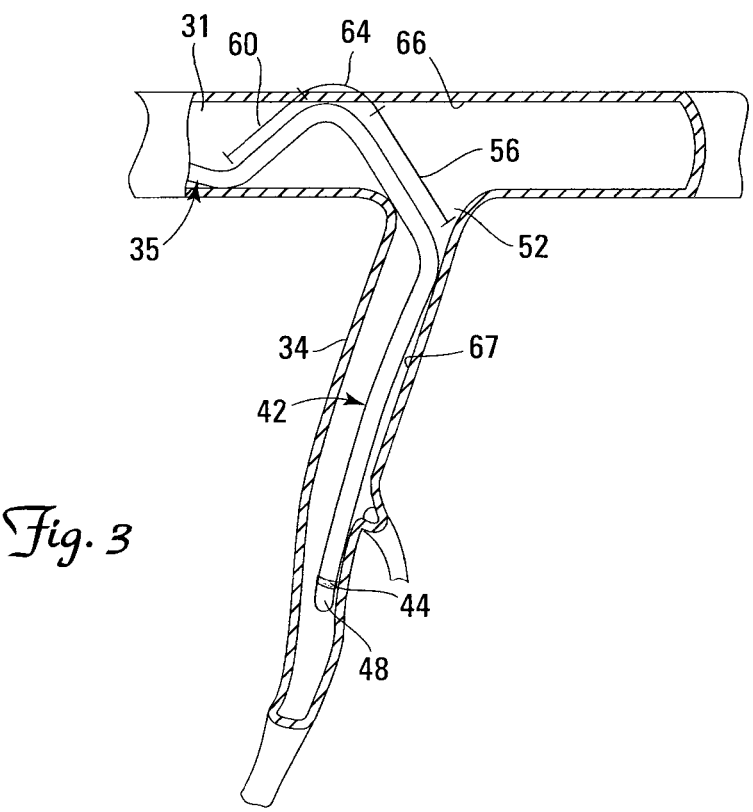
FIG. 3 is a partial cutaway view of the cardiac vessel illustrated in FIG. 2 showing a technique for fixation of the distal end of the lead in the cardiac vessel according to one embodiment of the present invention.

FIG. 3 illustrates the fixation function provided by stiffening the first, second, and third fixation portions 56, 60, 64 according to one embodiment of the present invention. As shown in FIG. 3, when in the stiffened state, the portions 56, 60 and 64, are constrained by a coronary sinus wall 66 and/or a branch vessel wall 67, thus preventing the distal end region 42 from being dislodged from the branch vessel 34 by the natural motion of the heart 20 and/or by forces exerted by the flow of blood from the branch vessel 34 into the coronary sinus 31. If desired, the portion of the lead distal to the fixation portion 56 can remain flexible, however, thus allowing this portion to move with the heart 20 during the cardiac cycle.

It will be appreciated that in some embodiments, the locations of the selected fixation portions 56, 60 and 64 along the lead 14 are generally determined based on the specific patient anatomy and the target branch vessel in which the lead 14 is partially implanted. In such embodiments, fixation is accomplished by deploying separate, implantable stiffening structures along the lead 14 so as to stiffen selected portions 56, 60, and/or 64. In other embodiments, discussed in detail below, one or more of the fixation portions 56, 60 and/or 64 has specific structures incorporated therein (e.g., within the lead body 35) at fixed locations along the lead 14 for stiffening the respective portion(s) of the lead 14.

Figure 4:
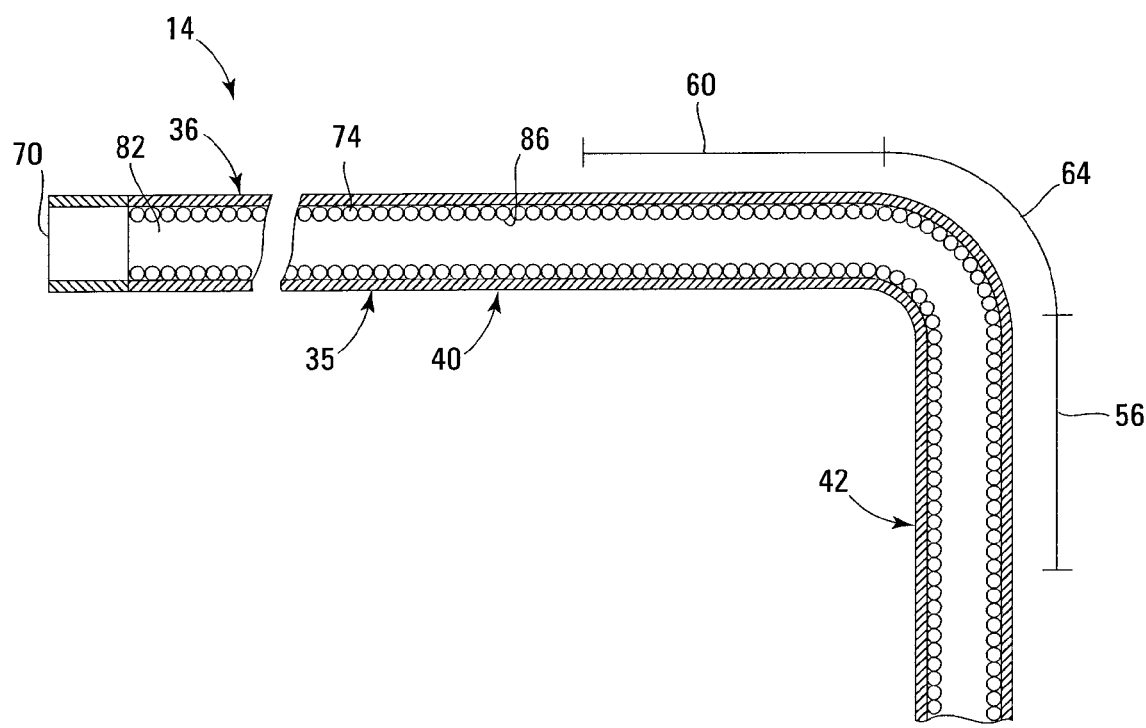
FIG. 4 is a partial cross-sectional view of a portion of the lead of FIG. 1.

FIG. 4 is a partial cross-sectional view of a portion of the lead 14 of FIG. 1, depicted as though in the implanted position of FIG. 2 with the distal end region 42 positioned in the branch vessel 34. As shown in FIG. 4, the lead 14 includes, in one embodiment, a proximal end 70, an insulated conductor 74 encapsulated by the lead body 35, and a lumen 82 defined by an inner wall 86. In the illustrated embodiment, the lumen 82 extends from the proximal end 70 beyond the first fixation portion 56. In other embodiments, the lumen 82 may be omitted, may extend only partially through the lead 14, or may extend all the way through the lead 14 through the distal tip 48 (see FIG. 1).

In the embodiment shown in FIG. 4, the conductor 74 is shown as a tightly spaced coil. Alternatively, the conductor 74 may be in the form of a conductive wire, thin ribbon, or a plurality of conductive wires formed as a cable. In FIG. 4, the wall 86 of the lumen 82 is formed by the inner surface of the conductor coil 74, although in other embodiments, a separate covering may form the wall 86. In some embodiments, the lead body 35 includes radio-opaque markers for use by the physician to identify the distance between the lead distal tip 48 and/or the electrode 44 and the entrance 52 to the branch vessel 34 (see FIG. 2).

Figure 5:
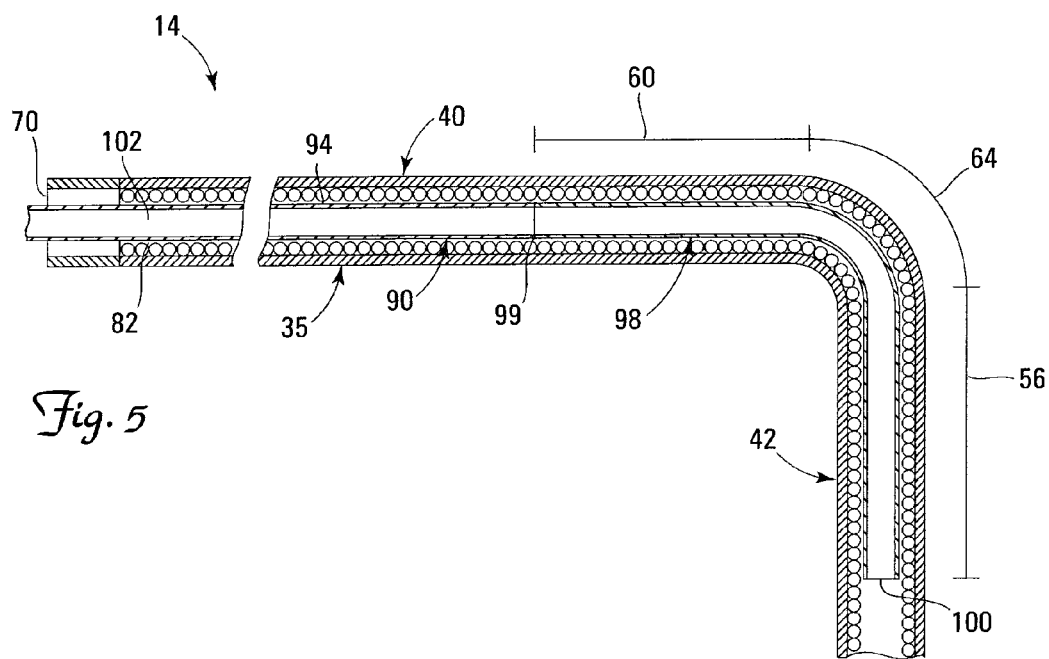
FIG. 5 is a partial cross-sectional view of a portion of a lead assembly including the lead of FIG. 1 with a stiffening structure for fixation of the lead according to one embodiment of the present invention.

FIG. 5 is a partial cross-sectional view of a portion of a lead assembly according to one embodiment of the present invention, including the lead 14 of FIG. 3 and an implantable stiffening member 90. As shown in FIG. 5, the implantable member 90 includes a proximal portion 94, a pre-curved distal portion 98 having a proximal end 99 and terminating in a distal end 100, and an internal channel 102. As shown, the implantable member 90 is adapted to be implanted within the lumen 82 of the lead 14 and coupled to the lead 14 with the pre-curved portion 98 generally within the first, second, and third selected fixation portions 56, 60, 64 of the lead 14.

The pre-curved distal portion 98 of the implantable member 90 is sufficiently stiff so as to stiffen the fixation portions 56, 60, and 64 of the lead 14 (i.e., change them from the flexible state to the stiffened state). When so stiffened, the fixation portions 56, 60, 64 will effectively prevent the distal end region 42 from being spontaneously displaced from the branch vessel 34, as in the manner described above. In one embodiment, the pre-curved portion 98 may have a stiffness equal to or greater than that of the lead 14 in the fixation portions 56, 60, 64. In one embodiment, the proximal portion 94 of the implantable member 90 is more flexible than the pre-curved portion 98, although this is not a requirement.

In the illustrated embodiment, the proximal portion 94 can extend to near or beyond the proximal end 70 of the lead when implanted as shown in FIG. 5. In one embodiment, the proximal portion 94 may be secured to the lead body 35. Because it extends to or near the proximal end 70 of the lead 14, the proximal portion 94 can also be accessed by the physician for removal and/or repositioning of the implantable member 90. Such removal of the implantable member 90 further allows for removal of the distal end region 42 from the branch vessel 34 and/or complete removal of the lead 14 from the patient's body if desired. In other embodiments, the proximal portion 94 of the implantable member 90 may be in the form of a flexible tether that can either be attached to the lead body 35 or can remain unattached. In some embodiments, the proximal portion 94 may be omitted. For example, the implantable member 90 may be coupled to the lead 14 merely by friction between its outer surface and the wall of the lumen 82. In still other embodiments, other structures and methods may be utilized to fix the position of the implantable member 90 and to facilitate its removal.

The implantable member 90 can have any structure providing the necessary pre-curved shape and sufficient rigidity to create the desired amount of fixation. In the illustrated embodiment, the implantable member 90 is shown having a tubular structure. In other embodiments, the implantable member 90 is an elongated coil. In other embodiments, the implantable member 90, or alternatively, the pre-curved portion 98, has a solid (i.e., non-tubular) structure. In still other embodiments, the implantable member 90 may include a combination of solid and tubular portions. Thus, it will be appreciated that the implantable member 90 need not have a continuous structure throughout.

The implantable member 90 may be made from any materials having the desired rigidity characteristics. In some embodiments, the implantable member 90 may be made substantially from metal (e.g., stainless steel, titanium or alloys thereof). In one embodiment, the implantable member 90, or at a minimum, the pre-curved portion 98, is made substantially from a shape memory alloy (e.g., Nitinol). In other embodiments, the implantable member 90 may be made substantially from a polymeric material such as, for example, polyetheretherketone (PEEK™). In some embodiments, the proximal and pre-curved portions 94 and 98 may be made from different materials to provide the desired relative flexibilities. Other suitable materials will be apparent to those skilled in the art based on the foregoing.

Figure 6A:
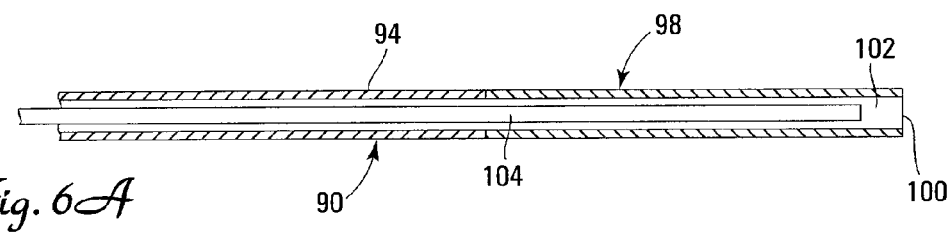
FIGS. 6A and 6B are cross-sectional views of the stiffening structure of FIG. 5.
Figure 6B:
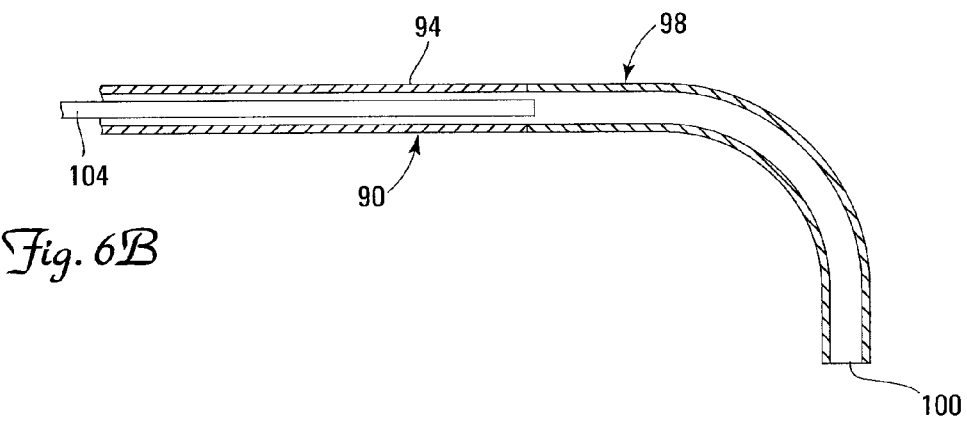

FIGS. 6A and 6B are cross-sectional views of a portion of the implantable member 90 of FIG. 5 shown with a core wire 104 disposed within the channel 102. As shown, the core wire 104 is relatively stiff compared to the pre-curved portion 98 of the implantable member 90 such that when the core wire 104 is extended through the pre-curved portion 98, the pre-curved portion 98 is substantially straightened to facilitate delivery of the implantable member 90 through the lumen 82 of the lead 14. As shown in FIG. 6B, when the core wire 104 is retracted proximally into the proximal portion 94 of the implantable member 90, the pre-curved portion 98 returns to its curved shape for fixation. In some embodiments, the implantable member 90 and/or the core wire 104 include length markers to assist the physician in locating the implantable member 90 at the appropriate position for fixation, as discussed below.

In one embodiment, as shown in FIGS. 6A and 6B, the implantable member 90 has an open distal end 100 such that the implantable member 90 can be deployed over the core wire 104, which in such embodiments can operate in a manner similar to a guide wire. In another embodiment, the implantable member 90 has a closed distal end 100, and the core wire 104 can push against this closed distal end 100 as the implantable member 90 and core wire 104 are advanced together through the lumen 82 of the lead 14.

Fixation of the distal end region 42 within the branch vessel 34 using the implantable member 90 can be accomplished as follows. Initially, the lead 14 is advanced transvenously until the distal end region 42 is positioned in the target branch vessel 34 according to methods known in the art. The implantable member 90 could be pre-loaded into the lumen 82 and retained near the proximal end 70 during deployment and positioning of the lead 14. Alternatively, the implantable member 90 may be loaded into the lumen 82 only after the lead 14 is delivered to the implanted position. Once the lead 14 is so positioned, the implantable member 90 is then advanced through the lumen 82 of the lead 14. In one embodiment, the core wire 104 is first advanced through the lumen 82 to operate as a guide wire for subsequent deployment of the implantable member 90. In another embodiment, in particular, one in which the distal end 100 of the implantable member 90 is closed or capped, the core wire 104 is inserted partially or completely into the channel 102, and the implantable member 90 and core wire 104 are advanced distally through the lumen 82 until the implantable member 90 is coupled to the lead 14 in the desired implantation position as shown in FIG. 5.

As mentioned above, the lead 14 and/or the implantable member 90 may, in some embodiments, include structures for identifying the proper position of the implantable member 90 for fixation. For example, in one embodiment, the lead body 35 includes radio-opaque markers by which the physician can, under fluoroscopy, determine the distance between the lead distal tip 48 and the branch vessel entrance 52. Additionally, the proximal portion 94 of the implantable member 90 and/or the core wire 104 may include length markers identifying the length of insertion of the distal end 100 of the implantable member 90. Because the length of the lead body 35 is also known, the physician can then determine the insertion length that will position the pre-curved portion 98 of the implantable member 90 in the correct location for fixation.

Figure 7:
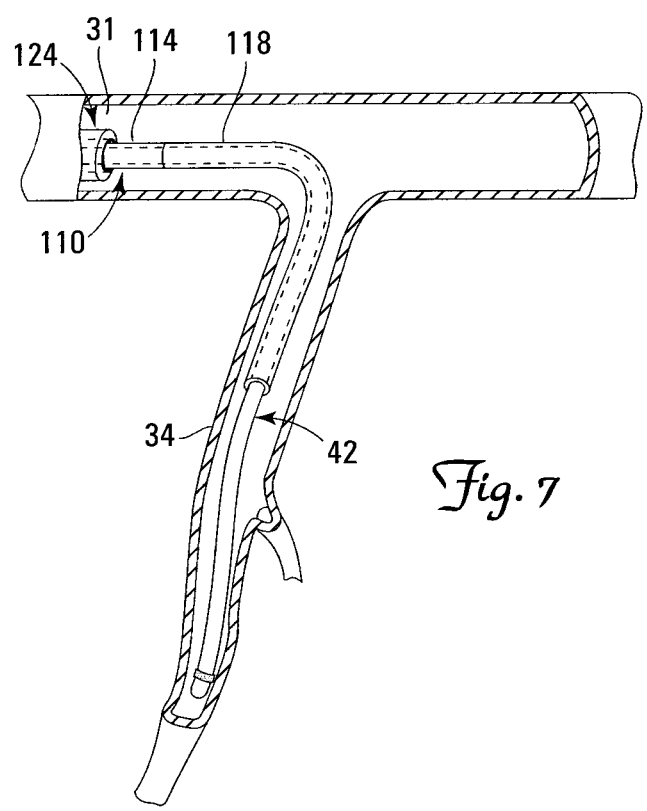
FIG. 7 is a partial cutaway view of a cardiac vessel showing a lead assembly in an implanted position and including a lead and an implantable stiffening sheath for fixation of the lead according to another embodiment of the present invention.

FIG. 7 is a partial cutaway view of the coronary sinus 31 and the branch vessel 34 showing an alternative lead assembly partially implanted therein and including the lead 14 and a tubular stiffening sheath 110 disposed over the lead 14. As shown in FIG. 7, the sheath 110 includes a proximal portion 114 and a pre-curved distal portion 118. The pre-curved portion 118 is sufficiently stiff so as to stiffen the fixation portions 56, 60, and 64 of the lead 14 (i.e., change them from the flexible state to the stiffened state). When so stiffened, the fixation portions 56, 60, 64 will effectively prevent the distal end region 42 from being spontaneously displaced from the branch vessel 34, as in the manner described above. In one embodiment, the pre-curved portion 118 has a stiffness equal to or greater than that of the lead 14 in the fixation portions 56, 60, 64. In one embodiment, the proximal portion 114 is more flexible than the pre-curved portion 118, although this is not a requirement.

Thus, in the implanted position shown in FIG. 7, the sheath 110 is disposed over the lead body 35 with the pre-curved portion 118 positioned to stiffen the fixation portions 56, 60, and 64 of the lead 14 such that an external proximally directed force is required to remove the distal end region 42 from the branch vessel 34. In the illustrated embodiment, the sheath 110 extends distally from a guide catheter 124 used to advance the sheath 110 over the lead body 35.

Figure 8:
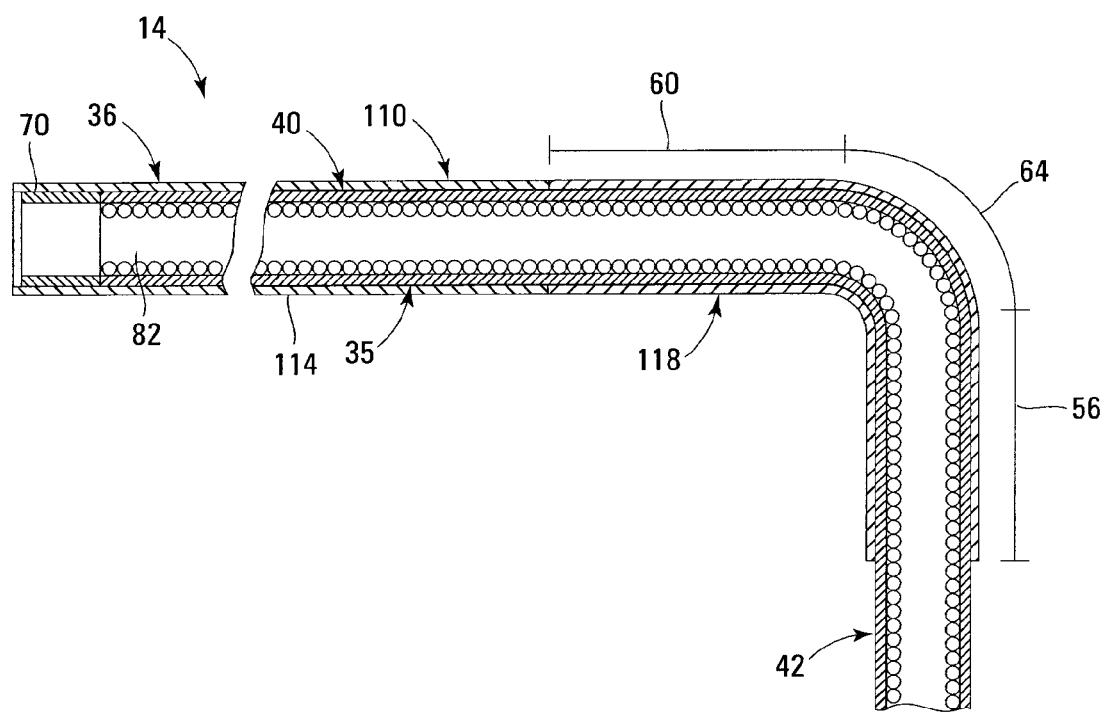
FIG. 8 is a partial cross-sectional view of a lead showing the sheath of FIG. 7 positioned over the lead body.

FIG. 8 is a partial cross-sectional view of a portion of the lead 14 with the sheath 110 positioned over the lead body 35 in the implanted position as shown in FIG. 7. As illustrated in FIG. 8, the proximal portion 114 of the sheath 110 extends to the proximal end 70 of the lead 14. It will be appreciated that the proximal portion 114 can also extend beyond the proximal end of the guide catheter 124 used for deployment of the sheath 110. In such embodiments, the proximal portion 114 provides structure for securing the sheath 110 in the desired location (e.g., via suture sleeves or other securing structure, not shown), and also provides structure that can be grasped by the physician to reposition and/or remove the sheath 110 if desired. In yet other embodiments, the proximal portion 114 may be omitted, and the sheath 110, consisting substantially only of the pre-curved portion 118, may be pushed into place using a push tube. In such embodiments, the sheath 110/pre-curved portion 118 may be permanently coupled to the lead 14 on the lead body 35, or alternatively, may include structures for engagement by a removal tool.

In one embodiment, the sheath 110 is made substantially or entirely of a polymer material. In one embodiment, the proximal portion 114 is made from a polymer material having a lower durometer than the materials used for the relatively stiff pre-curved portion 118. In one embodiment, the pre-curved portion 118 may be made of materials known in the art for use in pre-shaped catheters, including, without limitation, various polymers such as polyetheretherketone (PEEK™) polyether block amide (PeBax™). In yet another exemplary embodiment, the sheath 110 could include a flexible coil coated with a relatively rigid material (e.g., PEEK™ or PTFE) to form the pre-curved portion 118. Other materials and combinations of materials for the sheath 110 will be apparent to those skilled in the art based on the foregoing.

Figure 9A:
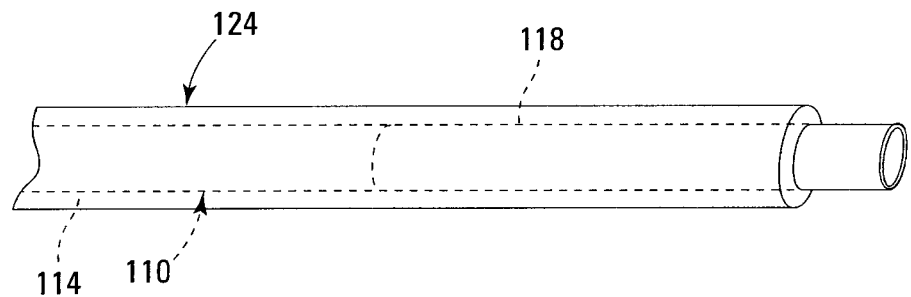
FIGS. 9A and 9B illustrate the sheath of FIG. 7 partially disposed within a guide catheter according to one embodiment for deploying the sheath over the lead body.
Figure 9B:
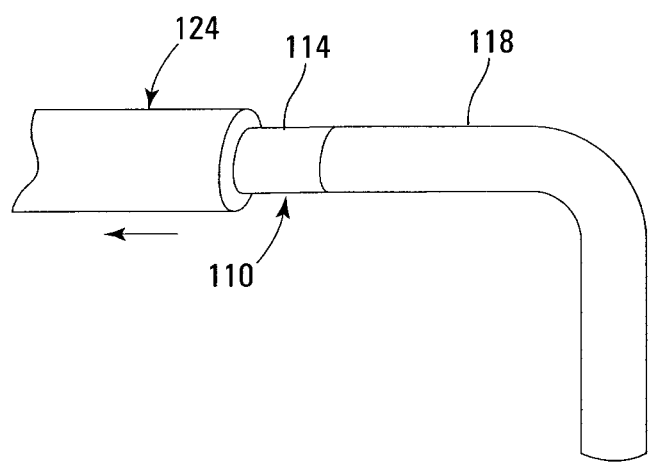

FIGS. 9A and 9B illustrate the sheath 110 partially disposed within the guide catheter 124 according to one embodiment for deploying the sheath 110 over the lead body 35 after implantation of the distal end region 42 of the lead 14 in the branch vessel 34. As shown in FIG. 9A, the guide catheter 124 is sufficiently stiff such that it can generally straighten the pre-curved portion 118 of the sheath 110 for delivering the sheath 110 to the desired implantation site. As shown in FIG. 9B, when the guide catheter 124 is retracted proximally, the pre-curved portion 118 returns to its pre-curved shape as shown in FIG. 7.

In operation, the lead 14 is first advanced transvenously until the distal end region 42 is positioned in the target branch vessel 34 according to methods known in the art. Once the lead 14 is so positioned, the sheath 110 is advanced over the lead body 35 to the desired position for fixation. In one embodiment, the guide catheter 124 is advanced over the lead body 35 until it extends distally into the branch vessel 34, and the sheath 110 is then advanced through the guide catheter 124 and over the lead body 35 to the implantation position. Alternatively, the sheath 110 may be inserted into the guide catheter 124 before advancing the guide catheter 124 over the lead body 35, in which case the sheath 110 and guide catheter 124 are advanced over the lead body together. Still alternatively, the sheath 110 may be pre-loaded onto the lead 14, but retained in a proximal location (i.e., near the proximal end 70) during delivery of the lead 14. In such a case, the lead 14 is advanced to the target branch vessel location, and the sheath 110 is then advanced to its implanted position for fixation, with the lead 14 held stable during deployment of the sheath 110.

The sheath 110 may include, in some embodiments, radio-opaque markers to assist in properly locating the sheath in the position illustrated in FIG. 7. Once the sheath 110 is properly positioned, the guide catheter 124 is retracted proximally to expose the pre-curved portion 118 of the sheath 110.

Figure 10:
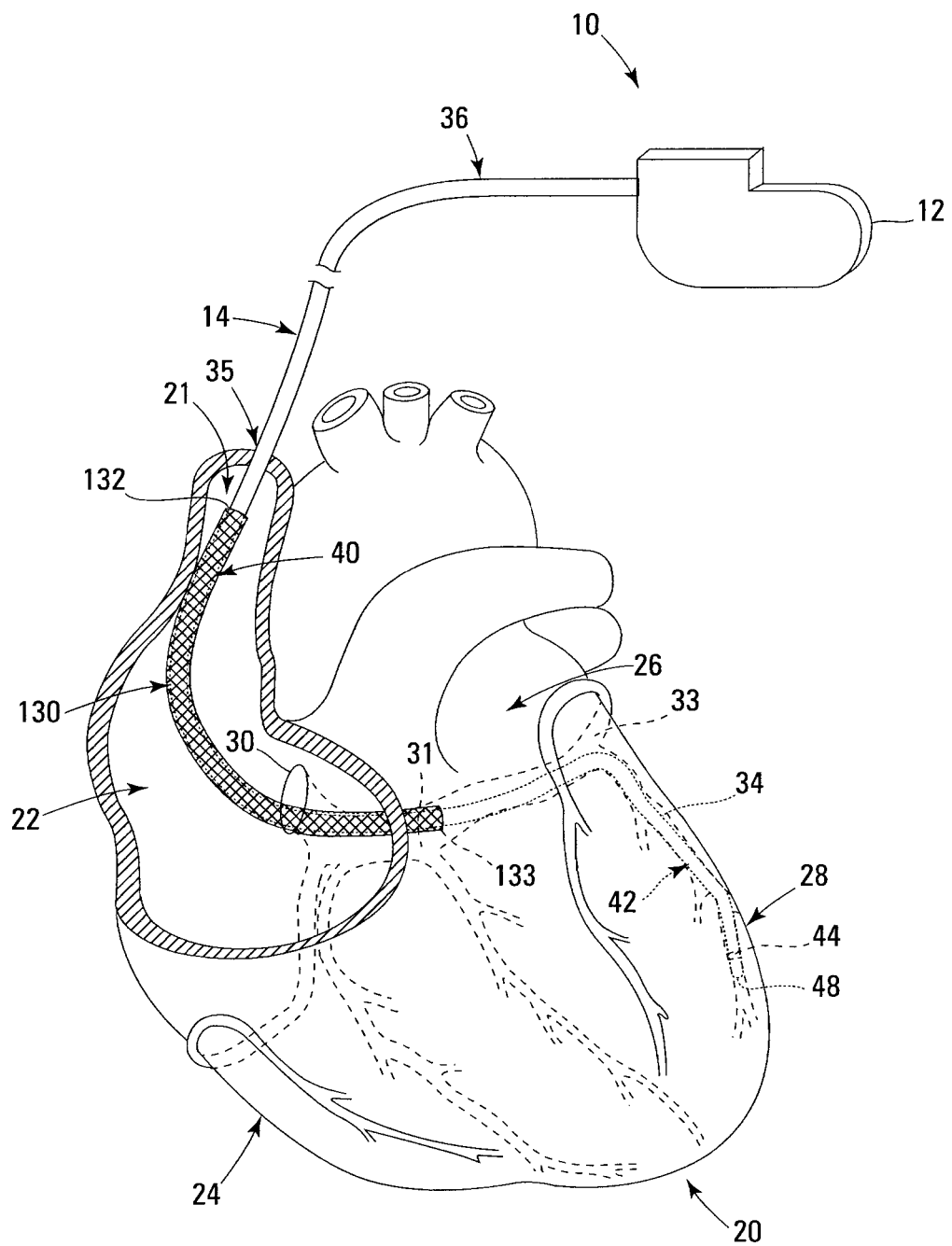
FIG. 10 is a partial cutaway view of the heart showing a lead partially deployed in the heart and including an implantable stiffening sheath according to another embodiment of the present invention.

FIG. 10 is a partial cutaway view of the heart 20 showing the lead 14 partially deployed therein and including a pre-curved implantable stiffening structure, which in the illustrated embodiment is a sheath 130 according to another embodiment of the present invention. As shown in FIG. 10 the sheath 130 includes a proximal end 132 and a distal end 133. The sheath 130 is adapted to be implanted over the lead body 54 with the proximal end 132 located in the superior vena cava 21 and the distal end 133 located in the coronary sinus 31 when the lead 14 is in the implanted position such as shown in FIG. 10.

The sheath 130 has a substantially continuous stiffness sufficient to stiffen the portion of the lead 14 extending from the superior vena cava 21 into the coronary sinus 31 as shown in FIG. 10. In one embodiment, the sheath 130 has a stiffness equal to or greater than that of the lead 14. As further shown, the sheath 130 has a pre-shaped curvature having a radius sufficient such that the lead 14 can contact and bear against the wall of the right atrium 22 and/or the superior vena cava 21. Thus, the contact between the wall of the right atrium 22 and/or the superior vena cava 21 and the stiffened portion of the lead 14 will prevent the lead 14 from being displaced proximally from its implanted position due to forces imposed by retrograde blood flow or natural heart motion.

The sheath 130 may be made of any materials known in the art for proving the desired stiffness and pre-curved shape. In the illustrated embodiment, the sheath 130 consists substantially of only a pre-curved segment, and can be deployed over the lead body 35 using, for example, a push tube as described above. In other embodiments, the sheath 130 may include a relatively flexible proximal portion similar to the sheath 110 described above. In such embodiments, the sheath 130 can, if desired, be used as a guide catheter for accessing the coronary sinus.

In other embodiments, the lead 14 may be fixed in place at the location and in the manner shown in FIG. 10 using an implantable member adapted to be deployed within a lead lumen. In such embodiments, the implantable member may have substantially the same structure as the implantable member 90 described above.

Figure 11:
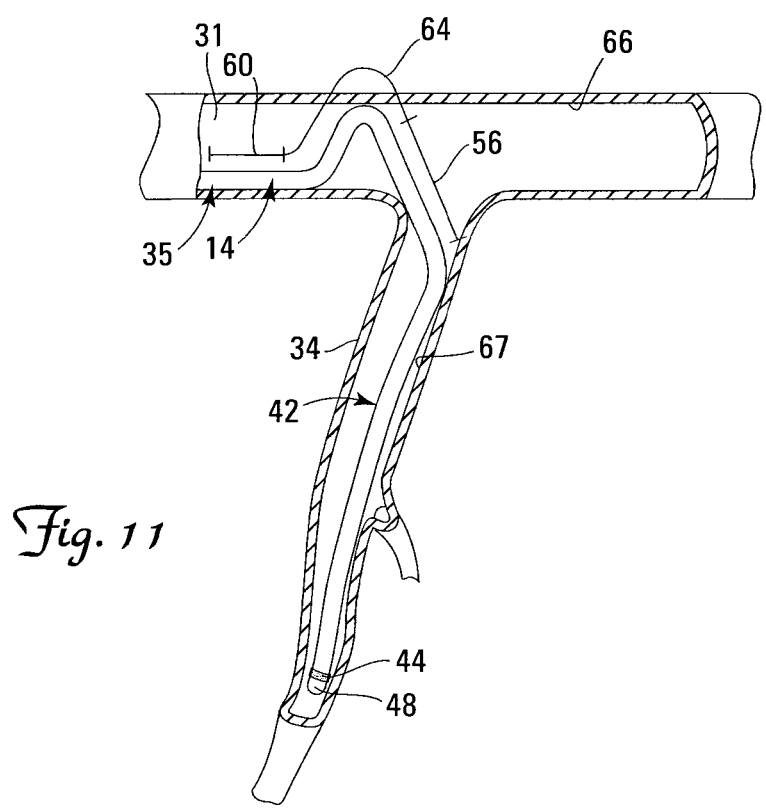
FIG. 11 is a partial cutaway view of a cardiac vessel showing an alternative embodiment for fixation of a portion of a lead within the cardiac vessel.

FIG. 11 is a partial cutaway view of the cardiac branch vessel 34 and the coronary sinus 31 showing an alternative embodiment for fixation of the distal end region 42 of the lead 14 within the cardiac branch vessel 34. As shown in FIG. 11, the first and second fixation portions 56 and 60 are relatively stiff (i.e., in the stiffened state), while the third portion 64 remains relatively flexible (i.e., as in the flexible delivery state). In this configuration, a force tending to push the distal end region 42 out of the branch vessel 34 will cause the first fixation portion 56 to push the third fixation portion 64 against the coronary sinus wall 66. At the same time, the first fixation portion 56 will be constrained by the branch vessel wall 67, and the relatively stiff second fixation portion 60 will constrain the amount by which the flexible third fixation portion 64 can bend and be displaced proximally.

Figure 12:
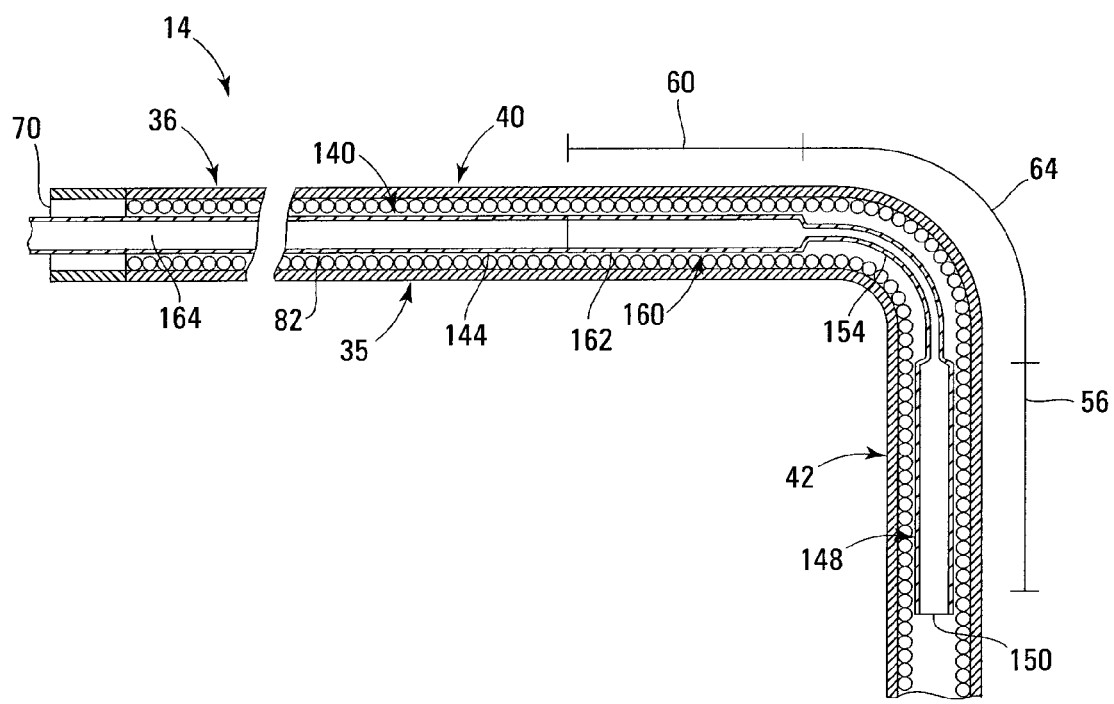
FIG. 12 is a partial cross-sectional view of a portion of a lead assembly including the lead of FIG. 1 and an alternative stiffening structure for fixation of a portion of the lead in a cardiac vessel in the manner illustrated in FIG. 11.

FIG. 12 is a partial cross-sectional view of a portion of a lead assembly including the lead 14 and an alternative stiffening structure, which in the illustrated embodiment is an implantable member 140, coupled to the lead 14 for fixation as illustrated in FIG. 11. As shown in FIG. 12, the implantable member 140 is disposed within the lumen 82 of the lead 14 and includes a proximal portion 144, a first stiff segment 148 having a distal end 150, a flexible segment 154, and a second stiff segment 160 having a proximal end 162. In the illustrated embodiment, the implantable member 140 is tubular and has a channel 164 throughout. The first and second stiff segments 148, 160 are configured to be stiffer than the flexible segment 154. The flexible segment 154 of the implantable member 140 may be more or less flexible than the lead 14, and in particular, the third fixation portion 64 of the lead 14.

As shown in FIG. 12, the implantable member 140 is adapted to be implanted within the lumen 82 of the lead 14 and selectively positioned such that the first stiff segment 148 is located within the branch vessel 34 with the second stiff segment 160 located proximal to the branch vessel entrance 52 and the flexible segment 154 extending through the branch vessel entrance 52 (see FIG. 11). The first and second stiff segments 148, 160 are configured to be sufficiently stiff so as to stiffen the fixation portions 56, 60 of the lead 14 (i.e., change them from the flexible state to the stiffened state) for fixation. In one embodiment, the first and second stiff segments 148, 160 may have a stiffness equal to or greater than that of the lead 14 in the fixation portions 56, 60. Thus, in the implanted state, the first and second stiff segments 148 and 160 operate to stiffen the fixation portions 56, 60 of the lead 14 (i.e., to change these portions from the flexible state to the stiffened state) for fixation of the distal end region 42 in the branch vessel 34. The flexible segment 154 may be configured such that it has a minimal effect on the flexibility of the third fixation portion 64 when positioned as shown in FIG. 11. This configuration will operate to prevent the distal end region 42 of the lead 14 from being pushed out of the branch vessel 34, as illustrated in FIG. 11. The relatively high flexibility of the flexible segment 159 permits this segment to bend through the transition from the coronary sinus 31 (or other primary vessel such as the great cardiac vein 33) and the branch vessel 34.

In the illustrated embodiment of FIG. 12, the implantable member 140 is shown as having a tubular structure. In this embodiment, the tube wall thickness of the stiff segments 148, 160 may be greater than that of the flexible segment 154, thus providing the desired relative flexibilities of the stiff and flexible segments. In other embodiments, the implantable member 140 may be an elongated coil in which the stiff segments 148, 160 have a larger outside diameter and/or are made of heavier wire than the flexible segment 154. Alternatively, the stiff segments 148, 160 and the flexible segment 154 may be made from different materials having different rigidity characteristics. In short, any structures or methods for providing the desired relative flexibilities of the stiff members 148, 160 and the flexible segment 154 can be used within the scope of the present invention. Additionally, the implantable member 140 may be made from any materials and combinations of materials providing the desired rigidity characteristics, including those materials described above with respect to the implantable member 90.

In one embodiment, the implantable member 140 is deployed within the lumen 82 of the lead 14 using a core wire (not shown in FIG. 12) similar to that used for the implantable member 90 described above. For example, the distal end 150 of the implantable member 140 may be capped such that a core wire can operate as a push member to push the implantable member 140 to the desired implantation location. In another embodiment, the channel 164 may have a reduced diameter portion (e.g., at the transition from the second stiff segment 160 to the flexible segment 154) or internal projection acting as a stop for the push member to bear against during deployment of the implantable member 140. In still other embodiments, the proximal portion 144 may be in the form of a relatively thin tether, and a push tube can be disposed over the tether to push against the first stiff segment 148 to deploy the implantable member 140.

Figure 13:
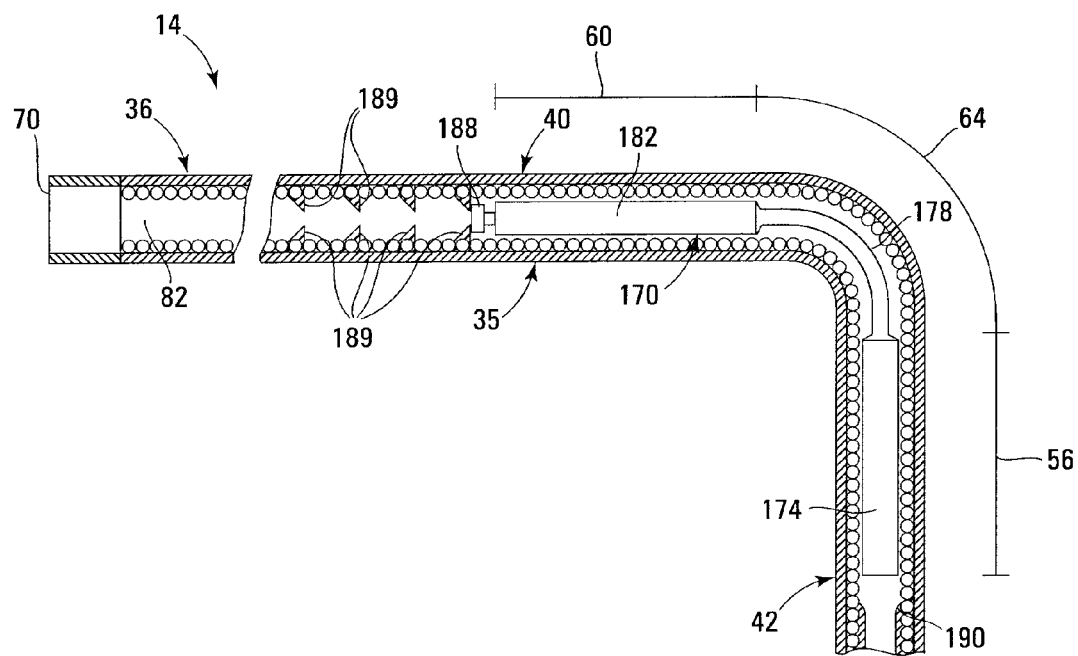
FIG. 13 is a partial cross-sectional view of a portion of a lead assembly including the lead of FIG. 1 and an alternative implantable stiffening structure for stiffening portions of the lead for fixation in the manner shown in FIG. 11.

FIG. 13 is a partial cross-sectional view of a portion of a lead assembly including the lead 14 and an alternative implantable stiffening member 170 implanted in the lumen 82 for stiffening the selected fixation portions 56, 60 of the lead 14 in the manner shown in FIG. 11. As shown in FIG. 13, the implantable member 170 includes a first stiff segment 174, a flexible segment 178, and a second stiff segment 182 which are otherwise similar in function to the corresponding portions of the implantable member 140 described above, except that the portions 174, 178 and 182 of the implantable member 170 are substantially solid throughout. It will be appreciated that in other embodiments not shown, the implantable member 170 may include combinations of solid and tubular portions.

In the embodiment illustrated in FIG. 13, the first and second stiff segments 174 and 182 are shown to be thicker than the flexible segment 178, thereby providing the desired differences in stiffness among the portions. In other embodiments, the portions 174, 178, and/or 182 may be made of different materials having different stiffness characteristics. In other embodiments, the flexible segment 178 may be made relatively flexible by placing kerfs or other structural features within the portion 178 to provide the desired flexibility.

As further shown in FIG. 13, the implantable member 170 includes a hub structure 188 in lieu of a proximal portion extending near the proximal end 70 of the lead 14 (as is shown in the implantable members 90 and 140 as illustrated and described above). The hub 188 provides a structure for engagement by a grasping tool to facilitate repositioning and/or removal of the implantable member 170 after implantation. It will be appreciated that any of the exemplary implantable stiffening structures described above (e.g., the implantable members 90, 140) may include similar structures in lieu of, or in addition to, proximal portions or tethers, for facilitating their repositioning and/or removal. It will further be appreciated that the solid implantable member 170 may also, in other embodiments include a proximal portion or tether (in addition to or in lieu of the hub 188) similar to the previously described embodiments.

In one embodiment, the implantable member 170 may be deployed within the lumen 82 using a push member for pushing against the hub 188. Alternatively, if the implantable member 170 includes a proximal tether in lieu of or in addition to the hub 188, the push member may be in the form of a push tube adapted to be disposed over the tether. Other devices and methods for advancing the implantable member 170 through the lumen 82 will be apparent to those skilled in the art.

As further illustrated in FIG. 13, the lead 14, in one embodiment, includes resilient ribs 189 and a stop 190 within the lumen 82 for securing the implantable member 170 in its implanted position for fixation. As shown in FIG. 13, the ribs 189 are disposed at spaced positions along the lumen 82, and are resilient and shaped to permit movement of the implantable member 170 in the distal direction, and to prevent subsequent movement in the proximal direction. Additionally, if removal of the implantable member 170 is desired, a removal tool can be inserted to deflect the ribs 189 to permit the implantable member 179 to be retracted. As further shown, the stop 190 is a reduced diameter portion of the lumen 82 having a diameter smaller than that of the stiff segment 174 of the implantable member 190, and operates to prevent distal movement of the implantable member 170 beyond a predetermined point. Other structures and techniques for securing the implantable member 170 in the desired position will be apparent. Furthermore, it will be appreciated that similar structures may be used in connection with the other implantable member embodiments described above.

The implantable member 170 may be made from any materials and combinations of materials providing the desired rigidity characteristics, including the materials described above with respect to the implantable members 90 and 140.

It will be appreciated that although the Figures illustrate the implantable members 90, 140, and 170 disposed within the main lumen 82 of the lead 14 (i.e., the lumen formed by the conductor 74), in other embodiments, the respective implantable members may be disposed within other lumens extending through, for example, the lead body 35.

Figure 14:
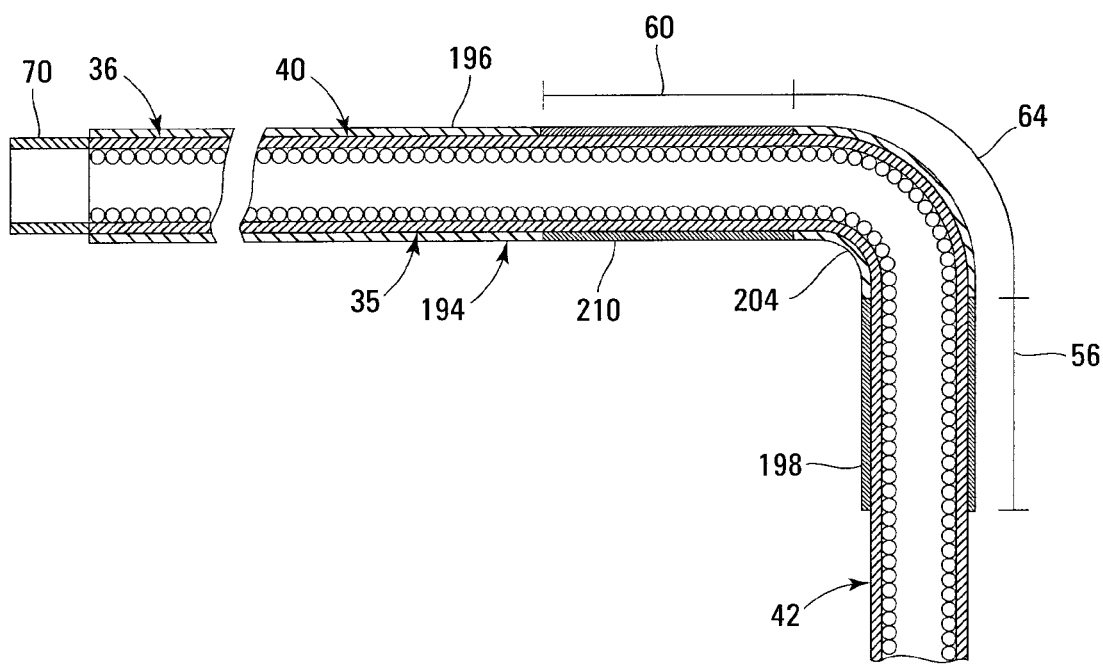
FIG. 14 is a partial cross-sectional view of a portion of a lead assembly including the lead of FIG. 1 and an alternative implantable stiffening structure according to another embodiment of the present invention.

FIG. 14 is a partial cross-sectional view of a portion of a lead assembly including the lead 14 and an alternative implantable stiffening structure, which in this embodiment is a tubular sheath 194 disposed over the lead body 35 for stiffening the first and second fixation portions 56, 60 of the lead 14 as shown in FIG. 11. As shown in FIG. 14, the tubular sheath 194 includes a proximal portion 196, a first stiff segment 198, a flexible segment 204, and a second stiff segment 210. As shown, the flexible segment 204 extends between the first and second stiff segments 198, 210.

The implantable member 194 is adapted to be implanted over the body 35 of the lead 14 and positioned such that the first stiff segment 198 is located in the branch vessel 34 with the second stiff segment 210 located proximal the branch vessel entrance 52 and the flexible segment 204 extending through the branch vessel entrance 52 (see FIG. 11). Thus, in the implanted state, the first and second stiff segments 198 and 210 operate to stiffen the selected fixation portions 56, 60 of the lead 14 (i.e., to change these portions from the flexible state to the stiffened state) for fixation of the distal end region 42 in the branch vessel 34. The flexible segment 204 may be configured such that it has a minimal effect on the flexibility of the third fixation portion 64. As with the implantable members 140 and 170 described above and as illustrated in FIG. 11, this configuration will operate to prevent the distal end region 42 from being pushed out of the branch vessel 34. The sheath 194 may be deployed over the body 35 of the lead 14 using, for example, a guide catheter as described above with respect to the tubular sheath 110.

In one embodiment, the sheath 194 is made substantially or entirely of a polymer material. In one embodiment, the flexible segment 204 is made from a polymer material having a lower durometer than the materials used for the first and second stiff segments 198, 210. In another embodiment, the portions 198, 204 and 210 may be made from the same material, with the flexible segment 204 including cuts or kerfs to provide the desired flexibility. In yet another exemplary embodiment, the sheath 194 could include a flexible coil coated with a relatively rigid material (e.g., PTFE) which is then etched or otherwise removed to form the flexible segment 204, with the remaining coated portions forming the stiff segments 198 and 210.

As with the sheath 110 described above, in some embodiments, the proximal portion 196 may be sized to extend to or near the proximal end 70 of the lead 14 and beyond the proximal end of the guide catheter used for deployment of the sheath 194. In such embodiments, the proximal portion 196 provides structure for securing the sheath 194 in the desired location (e.g., via suture sleeves or other securing structure), and also to provide access to the sheath 194 to facilitate removal of the sheath 110 if desired. In yet other embodiments, the proximal portion 196 may be omitted, and the sheath 194 may be pushed into place using a push tube. In such embodiments, the sheath 194 may permanently reside on the lead body 35, or alternatively, may include structures (e.g., a hub similar to the hub 188 of the implantable member 170 adapted for a tubular sheath) for engagement by a removal tool deployed through a guide catheter.

Figure 15A:
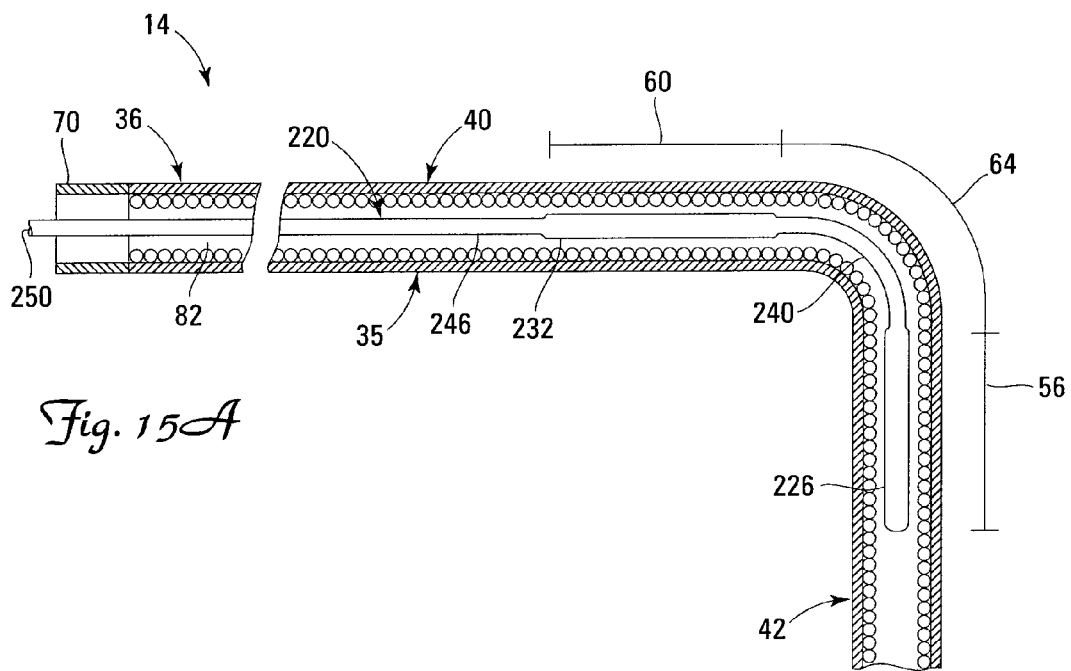
FIGS. 15A and 15B are partial cross-sectional views of a portion of a lead assembly including the lead of FIG. 1 and an implantable stiffening member according to another embodiment of the present invention.
Figure 15B:
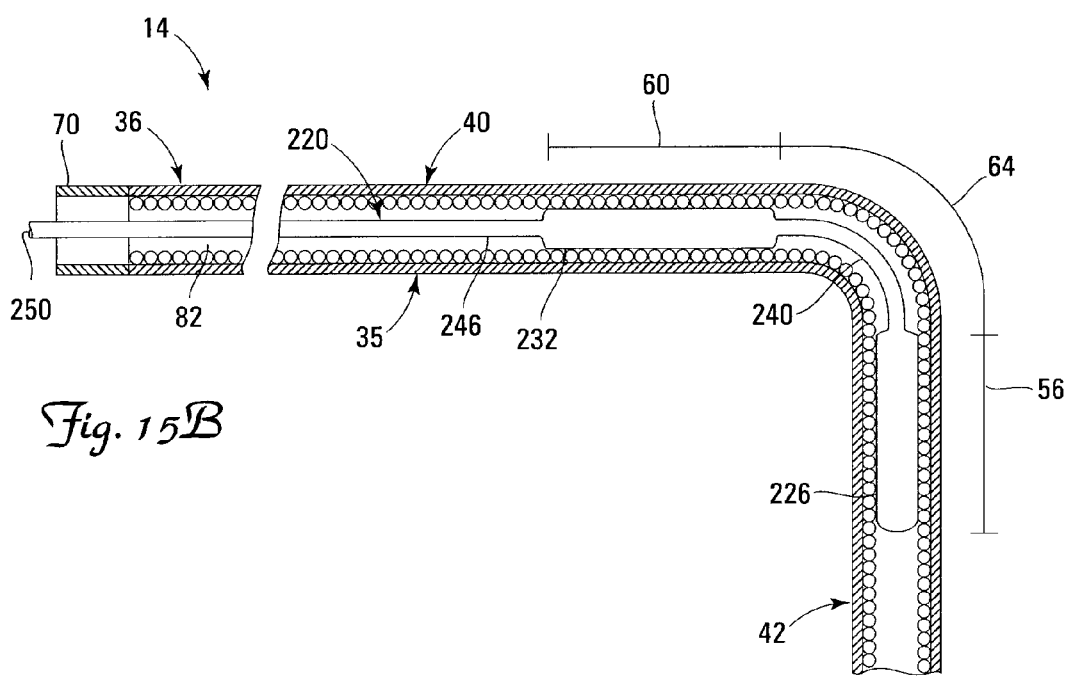

FIGS. 15A and 15B are partial cross-sectional views of a lead assembly including the lead 14 and an alternative implantable stiffening member 220 according to another embodiment of the present invention. As shown in FIG. 15A, the implantable member 220 includes first and second balloons 226 and 232, a first tube 240 fluidly connecting the balloons 226 and 232, and a second or proximal tube 246 extending proximally from the second balloon 232 and dimensioned to extend to the proximal end 70 of the lead 14. As shown, the proximal tube 246 includes a proximal opening 250. The balloons 226, 232 are adapted to contain a fluid and to change from a collapsed state for delivery to an expanded (i.e., inflated and pressurized) state for stiffening portions of the lead 14 distal and proximal, respectively, the branch vessel entrance 52. Thus, the balloons 226, 232, when so expanded, provide substantially the same stiffening function for fixation as the stiff segments 148 and 160 of the implantable member 140 described above. Similarly, the tube 240 may have substantially the same flexibility characteristics as, for example, the flexible segment 154 of the implantable member 140. FIG. 15A depicts the balloons 226, 232 in the collapsed delivery state, and FIG. 15B depicts the balloons 226, 232 coupled to the lead 14 in the expanded state for fixation. In one embodiment, the balloons 226, 232 can be returned to their collapsed states by withdrawing the fluid to permit repositioning and/or removal of the implantable member 220 if desired.

The tube 240 is in fluid communication with both balloons 226, 232, and the proximal tube 246 is in fluid communication with the second balloon 232 and provides a duct for filling and inflating the balloons 226, 232 with a fluid via the proximal opening 250. In one embodiment, the proximal tube 246 also includes a closure structure (not shown) for closing and sealing the proximal opening 250 to maintain fluid within the balloons 226, 232. The balloons 226, 232 may be filled with any fluids known in the art for filling balloon catheters and the like, including, for example, air and saline. In one embodiment, the balloons 226, 232 may be filled and inflated with a curable polymer such as, for example, polymethylmethacrylate (PMMA), which can be introduced in a liquid state and which subsequently hardens in place within the balloons 226, 232.

The illustrated embodiment of the implantable member 220 may be deployed within the lead lumen 82 using any of the delivery devices and methods described above with respect to the implantable members 140 and 170. In another embodiment, the balloons 226, 232 and channels 240, 246 are attached to the lead 14 (i.e., are not parts of a separate implantable member 220).

Figure 16:
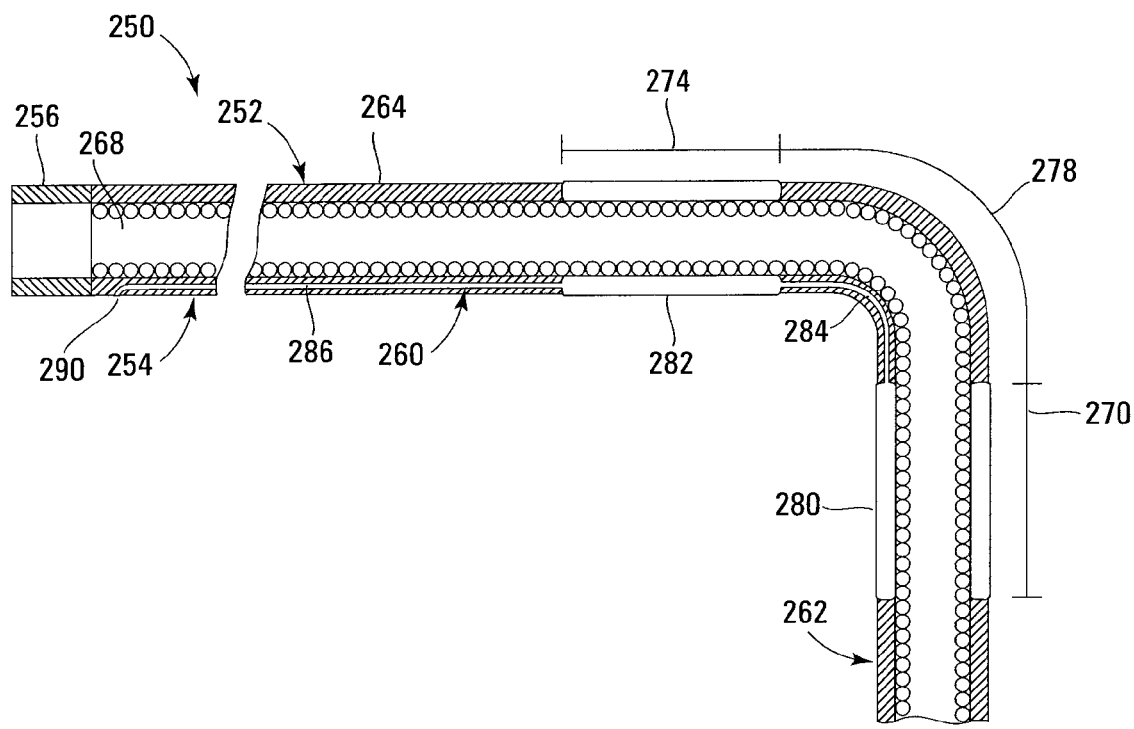
FIG. 16 is a partial cross-sectional view of a lead according to another embodiment of the present invention.

FIG. 16 is a partial cross-sectional view of a lead 250 according to another embodiment of the present invention. As shown in FIG. 16, the lead 250 includes an elongate body 252 defining a proximal region 254 with a proximal end 256, and a distal region 260 including a distal end region 262 adapted for implantation in a cardiac vessel such as described above. As further shown, the lead body 252 includes an outer insulating wall 264, and the lead 250 includes a lumen 268 extending from the proximal end 256 and at least partially through the distal end region 262. The lead 250 further includes first and second generally annular chambers 280, 282 incorporated into the lead body 252, a first channel 284 in fluid communication with the first and second chambers 280 and 282, and a second, proximal channel 286 in fluid communication with the second chamber 282 and including a proximal opening 290 near the proximal end 256 of the lead 250.

In the illustrated embodiment, the chambers 280, 282 are generally annular and extend circumferentially completely around the lead body 252. In other embodiments, one or both of the chambers 280, 282 may not extend completely circumferentially around the lead body 252. Additionally, in the illustrated embodiment, the channels 284 and 286 are disposed within the lead body 252. In other embodiments, the channels 284, 286 may be in the form of longitudinally-oriented tubes disposed within the lumen 268 of the lead 250.

The locations of the chambers 280, 282 define fixation portions 270, 274 of the lead 250 for fixation of the distal end region 262 in the manner illustrated in FIG. 11. The chambers 280, 282 are adapted to contain a fluid and to change from a collapsed, flexible state for delivery of the lead 250, to an expanded, stiffened state for fixation of the distal end region 262 in the target cardiac vessel. The chambers 280, 282 are further adapted to be located distal and proximal, respectively, the branch vessel entrance 52 (see FIG. 11). Thus, the chambers 280, 282, when so expanded, provide substantially the same stiffening function for fixation of the lead as, for example, the stiff segments 148 and 160 of the implantable member 140 described above.

The channels 284, 286 provide flow ducts for filling the chambers 280, 282 to thereby stiffen the lead body 252 as desired. As is apparent from FIG. 16, the fluid can be introduced into the proximal channel 286 via the proximal opening 290. Any of the fluids described above with respect to the implantable member 220 may be used to fill and stiffen the chambers 280, 282. Additionally, as with the implantable member 220 described above, the proximal channel 286 may, in some embodiments, include a closure structure for closing the proximal opening 290 to maintain fluid within the chambers 280, 282.

The chambers 280, 282 can be placed anywhere within the wall 264 of the lead body 252. For example, in one embodiment, the chambers 280, 282 may be located near the outer surface of the wall 264. Alternatively, the chambers 280, 282 may be centered within the wall 264. In still other embodiments the chambers 280, 282 may be located within a secondary lumen.

Figure 17:
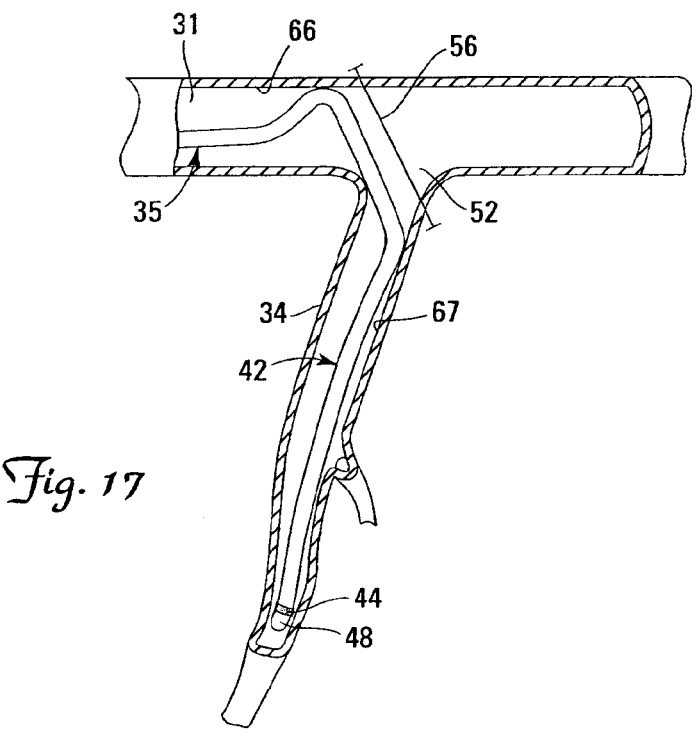
FIG. 17 is a partial cutaway view of a cardiac vessel showing an alternative technique for fixation of a portion of a lead within the cardiac vessel according to another embodiment of the present invention.

FIG. 17 is a partial cutaway view of the coronary sinus 31 and the cardiac branch vessel 34 showing an alternative embodiment for fixation of the distal end region 42 of the lead 14 within the cardiac branch vessel 34. As shown in FIG. 17, the first fixation portion 56 is in the stiffened state, while the remainder of the lead remains relatively flexible. As illustrated, a force tending to push the distal end region 42 out of the branch vessel 34 (e.g., retrograde blood flow or natural movement of the heart during the cardiac cycle) will cause the stiffened fixation portion 56 to push the lead body 35 into the wall 66 of the coronary sinus 31. Additionally, interference caused by the branch vessel wall 67 will prevent the stiffened portion 56 from being displaced through the branch vessel entrance 52.

Figure 18:
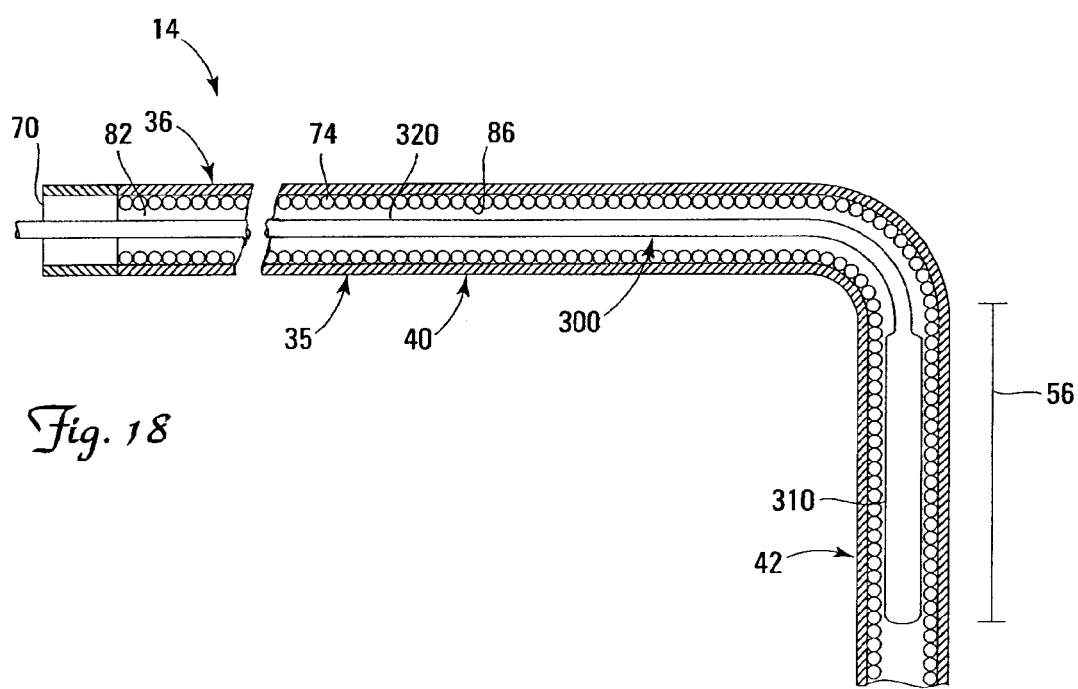
FIG. 18 is a partial cross-sectional view of a portion of a lead assembly including the lead of FIG. 1 and an implantable stiffening member for fixation of the lead in the manner illustrated in FIG. 17.

FIG. 18 is a partial cross-sectional view of a portion of a lead assembly including the lead 14 and an alternative implantable stiffening member 300 for fixation of the lead in the manner illustrated in FIG. 17. As shown in FIG. 18, the implantable member 300 is adapted to be located within the lumen 82, and includes a stiff segment 310 and a flexible segment 320 extending proximally from the stiff segment 310. As shown, the stiff segment 310 is adapted to be positioned within the lumen 82 in the distal end region 42 of the lead 14, such that the stiff segment 310 is located within the branch vessel 34 when in an implanted position. Thus, the stiff segment 310, when so positioned, stiffens the fixation portion 56 of the lead (see FIG. 17). As further shown, the flexible segment 320 is adapted such that it can extend to or proximally beyond the proximal end 70 of the lead 14 when the stiff segment 310 is located in the distal end region 42.

In the embodiment illustrated in FIG. 18, the stiff and flexible segments 310, 320 are shown to have substantially solid structures. It will be appreciated, however, that the stiff and flexible segments 310, 320 may have any structures providing the desired effect of stiffening the fixation portion 56 of the lead 14 so as to prevent spontaneous displacement of the distal end region 42 from the branch vessel in which it is implanted. For example, the stiff segment 310 may have any of the structures described above with respect to the stiff segments of the implantable members 90, 140, 170. Similarly, the flexible segment 320 may have any of the structures described above with respect to the flexible portions of the implantable members 90, 140, 170. In one embodiment, the stiff segment 310 may be in the form of a balloon, and the flexible segment 320 may be a channel for introducing a fluid into the balloon, such as described in connection with the implantable member 220. In other embodiments, the flexible segment 310 may be omitted.

As will be apparent to those skilled in the art, in other embodiments, the implantable member 300 may be in the form of a sheath having a stiff segment for implantation over the lead body. In such embodiments, the sheath may have any structure for providing the desired effect of stiffening the fixation portion 56 of the lead, including those structures described above in connection with the sheaths 110 and 194. Additionally, in other embodiments, the lead may be stiffened for fixation in the manner shown in FIG. 17 by including a chamber in the lead body itself adapted to contain a fluid, such as described above in connection with the lead 250. It will be appreciated that in such embodiments, no implantable member need be provided.

The stiff segment 310 is advantageously dimensioned so as to promote contact between the stiff segment 310 and the vessel walls 66, 67. For example, in the embodiment illustrated in FIG. 17, the stiff segment 310 desirably has a length sufficient to substantially prevent the stiffened portion 56 of the lead 14 from being maneuvered through the branch vessel entrance 52 and into the coronary sinus 31. In some embodiments, the stiff segment 310 may have a length of from about 1 cm to about 5 cm. In one embodiment, the stiff segment may have a length of about 2 cm. In other embodiments, the stiff segment 310 may have a length greater than 5 cm or less than 1 cm. Thus, the implantable stiffening member 300 can be provided in a variety of stiff segment lengths to accommodate variations in patient coronary anatomies and/or different implantation sites. Additionally, it will be appreciated that the same sizing considerations, and thus the same flexibility in stiffening structure sizing, are applicable to all of the other embodiments illustrated above.

It will further be appreciated, that the various embodiments of the present invention are not limited to use in the coronary vasculature. Rather, the fixation structures and methods of the present invention may be readily utilized for fixation of elongated leads and other implantable structures in other areas of the patient's vasculature (e.g., the pulmonary arteries).

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. An implantable medical electrical assembly, comprising:
an implantable pulse generator;
a medical electrical lead adapted to be directly connected at a proximal end to the implantable pulse generator and having a length sufficient to extend at least from an implantation location of the implanted medical device and into a branch vessel of a coronary sinus of a patient, the lead including:
a first region associated with the branch vessel; and
a second region associated with the coronary sinus; and
an implantable stiffening structure coupled to the lead, wherein at least a portion of the stiffening structure is located in a selected portion of the first region, wherein the stiffening structure is adapted to be selectively coupled to the lead after positioning the first region within the branch vessel and before the proximal end of the medical electrical lead is coupled to the implantable pulse generator.

2. The assembly of claim 1 wherein the stiffening structure includes a pre-curved portion having a first end and a second end, wherein the stiffening structure is coupled to the lead such that the first end of the pre-curved portion is located in the first region and the second end of the stiffening structure is located in the second region.

3. The assembly of claim 2 wherein:
the lead further includes a lumen extending from the proximal end through at least the selected portion of the first region; and
the stiffening structure is located within the lumen.

4. The assembly of claim 3 wherein the stiffening structure is generally tubular and has an internal diameter sized to receive a core wire for straightening the pre-curved portion for deployment of the stiffening structure within the lumen.

5. The assembly of claim 3 wherein the stiffening structure is made substantially from a polymeric or metallic material.

6. The assembly of claim 3 wherein the stiffening structure is made from a shape memory alloy.

7. The assembly of claim 2 wherein the stiffening structure is a sheath deployed over the lead.

8. The assembly of claim 7 wherein the sheath is made from a polymeric material.

9. The assembly of claim 1 wherein the stiffening structure includes:
a stiff segment coupled to the lead in the selected portion of the first region; and
a flexible portion extending from the stiff segment to a location proximate the proximal end of the lead.

10. The assembly of claim 1 wherein
the lead further includes a lumen extending from the proximal end through at least the selected portion of the first region; and
the stiffening structure is located within the lumen and includes:
a balloon coupled to the lead in the selected portion of the first region; and
a tube in fluid communication with the balloon and dimensioned to extend to a location proximate the proximal end of the lead.

11. The assembly of claim 1 wherein:
the lead further includes a lumen extending from the proximal end through at least the selected portion of the first region; and
the stiffening structure is located within the lumen and includes:
a first balloon coupled to the lead in the selected portion of the first region;
a second balloon coupled to the lead in a selected portion of the second region;
a first tube extending between and in fluid communication with the first and second balloons; and
a second tube in fluid communication with the second balloon and dimensioned to extend to a location proximate the proximal end of the lead.

12. The assembly of claim 1 wherein the stiffening structure includes:
a first stiff segment coupled to the lead in a selected portion of the first region;
a second stiff segment coupled to the lead in a selected portion of the second region; and a flexible segment extending between and connected to the first and second stiff segments.

13. The assembly of claim 12 wherein:
the lead further includes a lumen extending from the proximal end through at least the selected portion of the first region; and
the stiffening structure is located within the lumen.

14. The assembly of claim 12 wherein the stiffening structure is a sheath deployed over the lead.

15. An implantable medical electrical assembly, comprising:
an implantable pulse generator;
a medical electrical lead adapted to be directly connected at a proximal end to the implantable pulse generator and having a length sufficient to extend at least from an implantation location of the implanted medical device and into a branch vessel of a coronary sinus of a patient, the lead including:
a first region dimensioned to be implanted within the branch vessel; and
a second region dimensioned to be implanted within the coronary sinus; and
an implantable stiffening structure configured to be selectively coupled to the lead, wherein the stiffening structure is configured to be fixed along the first region after positioning the first region within the branch vessel and before the proximal end of the medical electrical lead is coupled to the implantable pulse generator.

16. The assembly of claim 15 wherein the stiffening structure includes a pre-curved portion having a first end and a second end, wherein the stiffening structure is configured to be coupled to the lead such that the first end of the pre-curved portion is located in the first region and the second end of the stiffening structure is located in the second region.

17. The assembly of claim 15 wherein:
the lead further includes a lumen extending from the proximal end through at least the selected portion of the first region; and
the stiffening structure is configured to be placed within the lumen.

18. The assembly of claim 15 wherein the stiffening structure is a sheath deployable over the lead.

19. The assembly of claim 15 wherein the stiffening structure includes:
a stiff segment configured to be coupled to the lead in the selected portion of the first region; and
a flexible portion configured to extend from the stiff segment to a location proximate the proximal end of the lead.

20. The assembly of claim 15 wherein the stiffening structure is configured to be selectively stiffened.

21. The assembly of claim 20 wherein the stiffening structure is selectively stiffened by inflation.

22. The assembly of claim 15 wherein the stiffening structure includes:
a first stiff segment configured to be coupled to the lead along the first region;
a second stiff segment configured to be coupled to the lead along the second region; and
a flexible segment extending between and connected to the first and second stiff segments.

23. An implantable medical electrical assembly, comprising:
an implantable pulse generator;
a medical electrical lead adapted to be directly connected at a proximal end to the implantable pulse generator and having a length sufficient to extend at least from an implantation location of the implanted medical device and into a branch vessel of a coronary sinus of a patient, the lead including:
a first region dimensioned to be implanted within the branch vessel; and
a second region dimensioned to be implanted within the coronary sinus; and
an implantable stiffening structure configured to be selectively coupled to the lead,
wherein the lead and the stiffening structure are configured such that the stiffening structure selectively stiffens one or both of the first region and the second region to secure the lead in the branch vessel, and
wherein the stiffening structure is configured to be selectively fixed to the lead after positioning the first region within the branch vessel and before the proximal end of the medical electrical lead is coupled to the implantable pulse generator.

* * * * *